(12) United States Patent
Jeglorz et al.

(10) Patent No.: US 9,649,025 B2
(45) Date of Patent: May 16, 2017

(54) SCANNING OPTICAL SYSTEM WITH MULTIPLE OPTICAL SOURCES

(71) Applicant: Wavelight GmbH, Erlangen (DE)

(72) Inventors: Tobias Jeglorz, Stein (DE); Christof Donitzky, Eckental (DE)

(73) Assignee: Wavelight GmbH (DE)

( * ) Notice: Subject to any disclaimer, the term of this patent is extended or adjusted under 35 U.S.C. 154(b) by 0 days.

(21) Appl. No.: 14/915,494

(22) PCT Filed: Sep. 2, 2013

(86) PCT No.: PCT/EP2013/068068
§ 371 (c)(1),
(2) Date: Feb. 29, 2016

(87) PCT Pub. No.: WO2015/028099
PCT Pub. Date: Mar. 5, 2015

(65) Prior Publication Data
US 2016/0213247 A1    Jul. 28, 2016

(51) Int. Cl.
*A61B 3/14* (2006.01)
*A61B 3/10* (2006.01)
*G01B 11/24* (2006.01)
*G01B 11/245* (2006.01)
*G02B 26/10* (2006.01)
*A61B 3/11* (2006.01)
*G01B 9/02* (2006.01)
*G02B 26/12* (2006.01)

(52) U.S. Cl.
CPC ............ *A61B 3/1025* (2013.01); *A61B 3/102* (2013.01); *A61B 3/1005* (2013.01); *A61B 3/111* (2013.01); *A61B 3/14* (2013.01); *G01B 9/02091* (2013.01); *G01B 11/245* (2013.01); *G01B 11/2441* (2013.01); *G02B 26/101* (2013.01); *G02B 26/105* (2013.01); *G02B 26/123* (2013.01)

(58) Field of Classification Search
CPC ......... A61B 3/14; A61B 3/0025; A61B 3/102; A61B 3/0008; A61B 3/1225; A61B 5/0066; G01B 9/02091; G01B 9/02027; G01B 11/0675
USPC ....................................................... 351/206
See application file for complete search history.

(56) References Cited

U.S. PATENT DOCUMENTS

2007/0189664 A1    8/2007  Andersen et al.
2010/0097682 A1    4/2010  Angeley et al.
2011/0043661 A1    2/2011  Podoleanu
(Continued)

OTHER PUBLICATIONS

Maciej Wojtkowski; "HIgh-speed optical coherence tomography: basics and applications"; Applied Optics, Optical Society of America, Washington, DC, USA; vol. 49; No. 16; Jun. 1, 2010; pp. D30-D61; ISSN: 0003-6935.
(Continued)

*Primary Examiner* — Mahidere Sahle

(57) ABSTRACT

In an embodiment, a scanning optical system comprises first and second optical sources and a deflector device. The first and second optical sources provide first and second beams, respectively, of optical radiation. The deflector device is disposed to receive and deflect the first and second beams, and is configured for a scanning operation on a beam of radiation traversing the deflector device. The first beam is incident on the deflector device with a first orientation and the second beam is incident on the deflector device with a second orientation that is different from the first orientation.

8 Claims, 1 Drawing Sheet

(56) References Cited

U.S. PATENT DOCUMENTS

Figure 1:
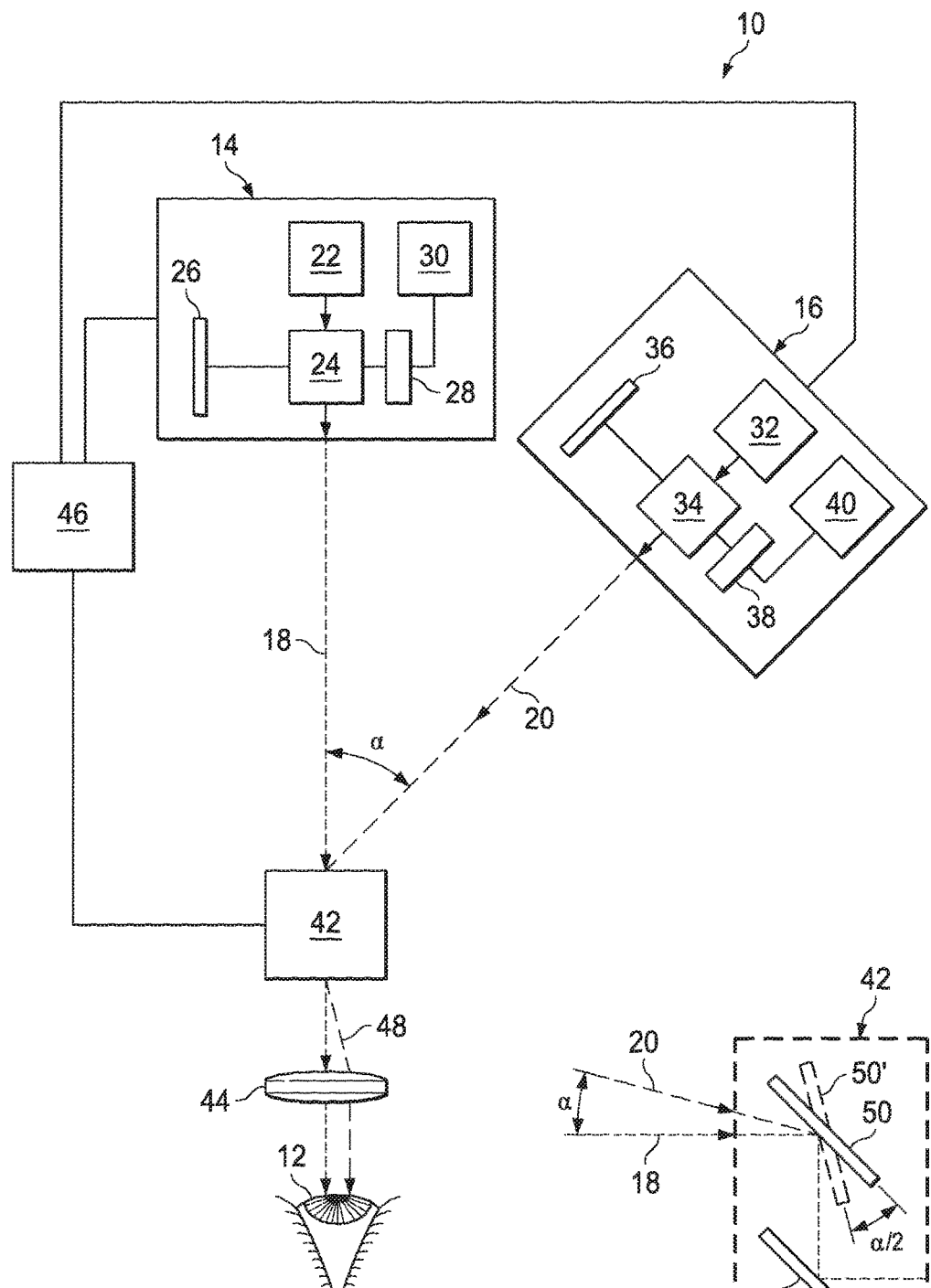

2011/0299038 A1 12/2011 Antkowiak et al.
2013/0163003 A1 6/2013 Massow et al.

OTHER PUBLICATIONS

Rohrer K et al.; "Comparison and Evaluation of Ocular Biometry Using a New Noncontact Optical Low-Coherence Reflectometer"; Ophthalmology, J.B. Lippincott Co.; Philadelphia, PA, USA; vol. 116; No. 11; Nov. 1, 2009; pp. 2087-2092; ISSN: 0161-6420.

SCANNING OPTICAL SYSTEM WITH MULTIPLE OPTICAL SOURCES

CROSS REFERENCE TO RELATED APPLICATIONS

This application is a section 371 national stage phase of International Application No. PCT/EP2013/068068, filed 2 Sep. 2013, titled "SCANNING OPTICAL SYSTEM WITH MULTIPLE OPTICAL SOURCES," which is hereby incorporated by reference in its entirety.

The present disclosure is concerned with a scanning optical system having multiple optical sources, wherein each optical source provides a respective beam of optical radiation. In certain embodiments, the multiplicity of optical sources includes a first optical source and a second optical source. It is to be understood that the present disclosure is not limited to a total of two optical sources. Instead, the multiplicity may include more than two optical sources, e.g., three or four.

As used herein, optical radiation refers to electromagnetic radiation in any of the ultraviolet, visible, and infrared wavelength ranges. The optical radiation provided by different one of the sources may be in different wavelength ranges or may have the same wavelength or wavelengths.

The scanning optical system may perform one or more applications that require a beam of optical radiation to be steered across a plane that is orthogonal to a direction of propagation of the beam (i.e. transverse scanning). Such steering may be needed in order to move the beam over a target area. Depending on the application and the radiation properties of the beam, incidence of the beam on the target may either serve to process (for example, ablate or photodisrupt) the target or serve to perform measurements on the target. A scanning optical system within the scope of the present disclosure may implement exclusive processing applications, exclusive measurement applications, or a combination of processing and measurement applications. For beam scanning, the scanning optical system comprises a deflector device that is disposed to receive and deflect a beam of optical radiation through various scan angles.

In a scanning optical system of the type envisaged by the present disclosure, the beams provided by the different sources traverse the deflector device. Depending on the mode of operation, the deflector device may perform scanning on a beam traversing the deflector device or may remain idle. In the latter case, the beam traverses the deflector device without being scanned. Whether scanned or not, all beams of the system may be guided along a common beam path from the deflector device to a beam output port (or "window") of the scanning optical system.

To ensure that the beams provided by the system pass through the deflector device, it may be envisaged to lead the beams together before the deflector device so that they propagate along a common optical axis and enter into the deflector device on this axis. Semi-transparent mirrors, flip mirrors, and polarization-dependent couplers are examples of coupling elements that are conventionally used to couple separate to beam paths onto a common optical axis. Unfortunately, the use of this type of coupling elements may cause certain drawbacks. For example, a semi-transparent mirror may cause a decrease in power of a beam traveling through the mirror. The use of a flip mirror may introduce undesired delays in the operation of the scanning optical system due to the time required for an actuator to rotate the flip mirror into and out of a beam path. Moreover, the provision of the coupling element means an increased complexity of the system and may make the initial setting of the system and later corrections of the setting more burdensome.

The present disclosure provides a scanning optical system, comprising: a plurality of optical sources, each optical source configured to provide a beam of optical radiation; a deflector device disposed to receive and deflect the beams provided by the optical sources, the deflector device configured for a scanning operation on a beam of radiation traversing the deflector device, wherein the beams provided by the optical sources include a first beam that is incident on the deflector device with a first orientation and a second beam that is incident on the deflector device with a second orientation, wherein the first orientation is different from the second orientation. In certain embodiments, the plurality of optical sources is two. In other embodiments, the plurality of optical sources is three. In yet other embodiments, the plurality of optical sources is four or more. In the scanning optical system according to the present disclosure, the deflector device is configured to receive the first and second beams (and possibly additional beams of optical radiation which may be provided by the system) at respective different orientations. As used herein, orientation refers to the direction of propagation of a beam when it reaches the deflector device. In certain embodiments, the first orientation is inclined with respect to the second orientation. An inclination angle of the first beam with respect to the second beam may be, e.g., not larger than 70, 60 or 50 degrees and/or not smaller than 1, 2, 3, 4, 5, 7, 10, 15 or 20 degrees. The first and second beams may have the same position of incidence or different positions of incidence on the deflector device.

The deflector device may include any suitable type of deflection element that can scan an incoming beam arriving with different orientations relative to the deflection element. According to certain embodiments, the deflector device includes a first scanning mirror disposed for tilting about at least one tilt axis, wherein the first beam is incident on the first scanning mirror with the first orientation and the second beam is incident on the first scanning mirror with the second orientation. The first scanning mirror may be a uni-axial mirror or a bi-axial mirror. The uni-axial mirror can be tilted about a single axis, the bi-axial mirror can be tilted independently about two mutually orthogonal axes. According to alternative embodiments, the deflector device includes a polygon scanner or an electro-optical crystal scanner, wherein the polygon scanner or electro-optical crystal scanner is capable of scanning an incoming beam arriving with different orientations relative to the scanner.

According to certain embodiments, the deflector device includes an electromagnetic drive unit for driving the first scanning mirror through an angular range that is larger than an angular offset between the first and second orientations. Angular offset means the value of an angle enclosed between the first and second orientations.

According to certain embodiments, the deflector device includes a first scanning mirror disposed for tilting about a first tilt axis and a second scanning mirror disposed for tilting about a second tilt axis, wherein the first tilt axis is oriented perpendicularly to the second tilt axis, wherein the first and second beams are incident on the first scanning mirror with the first and second orientations, respectively, wherein the first scanning mirror is arranged to direct the first and second beams to the second scanning mirror with a common, third orientation.

According to certain embodiments, the scanning optical system comprises an interferometric measuring device for analyzing a target optically. The measuring device is arranged to establish interference between radiation backscattered from the target to and reference radiation obtained from at least one of the beams provided by the optical sources. The measuring device may include at least one of an OLCR-based measuring unit and an OCT-based measuring unit.

Figure 2:
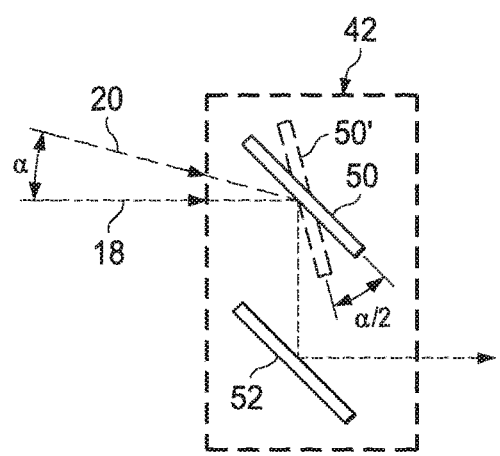

Certain embodiments will be described hereinafter in more detail with reference to the accompanying drawings, in which:

FIG. 1 illustrates schematically a scanning optical system according to an example configuration; and FIG. 2 illustrates details of a deflector unit of the system of FIG. 1 according to an example embodiment.

Referring now to the drawings, example embodiments of the disclosed apparatus and method are shown in detail. The following description is in no way intended to be exhaustive or to otherwise limit or restrict the accompanying claims to the specific embodiments shown in the drawings and disclosed herein. Although the drawings represent possible embodiments, the drawings are not necessarily to scale and certain features may be simplified, exaggerated, removed, or partially sectioned to better illustrate the embodiments. In addition, certain drawings may be in schematic form.

FIG. 1 illustrates a scanning optical system generally designated 10. The scanning optical system 10 is designed for performing diagnostic measurements on a human eye 12. Such measurements may be needed before, during, and/or after a laser-surgical treatment of the eye 12. The scanning optical system 10 includes first and second interferometric measurement units 14, 16 configured to perform low coherence interferometry using reference light provided by a light source inside the respective measurement unit and sample light derived from backscattered light reflected from the eye 12. In the illustrated example embodiment, two measurement units 14, 16 are shown. It is to be understood that any plurality of measurement units may be included with the scanning optical system 10. Moreover, the scanning optical system 10 may include a laser source module (not shown) in addition to the measurement units 14, 16, or in place of one of the measurement units 14, 16. When equipped with a laser source module, the scanning optical system 10 may be used as a combined diagnostic and surgical tool allowing both diagnostic measurements of the eye 12 as well as laser treatment of the eye 12 such as, e.g., for refractive correction of the eye 12.

The first measurement unit 14 emits a first beam 18 of optical radiation, and the second measurement unit 16 emits a second beam 20 of optical radiation. In certain embodiments, the first beam 18 and the second beam 20 have different wavelengths. In other embodiments, the first beam 18 and the second beam 20 have the same wavelength. The first measurement unit 14 implements, for example, an optical biometry device operating on the basis of optical low-coherence reflectometry (OLCR). The first measurement unit 14 may implement one or more non-contact, one-dimensional biometric functions including, but not limited to, a function for measuring the axial length of the eye 12, a function for measuring the central thickness of the cornea of the eye 12, a function for measuring the axial length of the anterior chamber of the eye 12, a function for measuring the central thickness of the crystal lens of the eye 12, a function for performing a keratometry (i.e. for measuring the anterior corneal curvature) of the eye 12, a function for measuring a white-to-white distance of the eye 12, a function for performing a pupillometry (i.e. for measuring the pupil diameter) of the eye 12, a function for measuring the eccentricity of a visual axis of the eye 12, and a function for measuring a retinal thickness of the eye 12.

The radiation of the first beam 18 may be in a red or infrared wavelength range and may, for example, be anywhere between 750 nm and 900 nm. As a purely illustrative and non-limiting example, the first beam 18 may have a wavelength of about 820 nm. The second measurement unit 16 may implement a two-dimensional or three-dimensional imaging device operating on the basis of optical coherence tomography (OCT). The radiation of the second beam 20 may be in a red or infrared wavelength range and/or in an UV wavelength range. For example, the second beam 20 may include radiation having a wavelength anywhere between 750 nm and 900 nm and/or anywhere between 750 nm and 300 nm. As a purely illustrative numerical example, the second beam 20 may have a wavelength of about 790 nm and/or about is 350 nm.

In certain embodiments, the first measurement unit 14 includes a first optical source 22, a first beam splitter 24, a first reference mirror 26, a first detector 28 and a first software-based analyzer 30 coupled as shown. The first detector 28 detects light resulting from interference of reference light reflected from the first reference mirror 26 with backscattered light (or "sample light") reflected from the eye 12 and returned to first the measurement unit 14. The first analyzer 30 evaluates the detection signals from the first detector 28 in a manner defined by desired functionality of the measurement unit 14. Similarly, the second measurement unit 16 includes a second optical source 32, a second beam splitter 34, a second reference mirror 36, a second detector 38 and a second software-based analyzer 40.

The scanning optical system 10 further comprises a deflector device 42, a focusing objective 44 and a control computer 46 coupled as shown. The deflector device 42 is configured to transversely scan an incoming beam (such as, e.g., the first beam 18 and/or the second beam 20) through a range of scan angles under control of a scan program executed by the control computer 46. Transverse scanning means a scanning operation in a direction transverse to the direction of propagation of the beam. By so scanning, the beam can be moved in one or two dimensions over a target area of the eye 12. A scanned beam as output from the deflector device 42 is shown by way of a dashed line 48 in FIG. 1.

The focusing objective 44 focuses an incoming beam to a point on the anterior surface of the eye 12 or within the eye 12. The focusing objective 44 may be a single-lens device or a multi-lens device. In certain embodiments, the focusing objective 44 may be omitted.

The control computer 46 controls operation of the measurements units 14, 16. In particular, the control computer 46 instructs the measurement units 14, 16 to commence and halt beam generation in accordance with diagnostic needs as defined by a control program and/or a user input of a surgeon. In general, only one of the measurement units 14, 16 will be active at a time, so that only one of the first and second beams 18, 20 is incident on the deflector device 42 at a time. At least one of measurement units 14, 16 requires scanning of its beam by the deflector device 42. For example, the OCT measurement unit 20 may require scanning of the second beam 20 in order to generate one or more slice-images of the eye 12. In contrast, the OLCR measurement unit 14 may not require scanning of the first beam 18. Therefore, in certain embodiments the control computer 46 controls the deflector device 42 to perform beam scanning during operation of one of the measurement units 14, 16 and to remain inactive, or immobile, during operation of the other of the measurement units 14, 16. In alternate embodiments, all measurement units 14, 16 (or in more general terms: all beam generating units of the scanning optical system 10) may require beam scanning for their operation.

As can be seen from FIG. 1, the first beam 18 and the second beam 20 are incident on the deflector device 42 with different orientations. In other words, the first beam 18 and the second beam 20 propagate along different axes when they arrive at the deflector device 42. More specifically, the propagation axes of the first and second beams 18, 20 are inclined with respect to each other by an angle α of less than 90 degrees before the beams 18, 20 enter into the deflector device 42. The deflector device 42 is a type that is adapted to accept an incoming beam from different input directions and output the beam in the same output direction irrespective of the input direction. In brief, the deflector device 42 may be referred to as a multi-path scanner.

FIG. 2 shows in greater detail an example configuration of the deflector device 42. As shown, the deflector device 42 includes first and second uni-axial scanning mirrors 50, 52. In certain embodiments, the mirrors 50, 52 can be tilted about mutually perpendicular tilt axes to enable two-dimensional scanning of a beam incident on the deflector device 42. An incoming beam is reflected from the first mirror 50, directed to the second mirror 52 and then reflected from the second mirror 52. Galvanometer drives (not shown) controlled by the control computer 46 may be provided for rotationally driving the mirrors 50, 52. Other types of drives than galvanometers and/or other types of deflecting element (such as an adaptive mirror) are equally conceivable.

At least one of the mirrors 50, 52 (the first mirror 50 in the illustrated example scenario) can be adjusted by means of its drive about its tilt axis to receive an incoming beam from different directions and direct the incoming beam to the same point on the second mirror 52, so that the beam can leave the deflector device 42 on the same optical axis. FIG. 1 illustrates by way of solid lines a situation in which the first beam 18 is incident on the deflector device 42 and illustrates by way of dashed lines a situation in which the second beam 20 is incident on the deflector device 42. The first and second beams 18, 20 arrive at the deflector device 42 with a mutual angular offset equal to the value of α. Depending on the mode of operation of the scanning optical system 10 (i.e. whether the first measurement unit 14 or the second measurement unit 16 is active), the control computer 46 can drive the first mirror 50 into different pre-defined initial positions corresponding to the respective operation mode, wherein the different initial positions are angularly displaced from each other by the value of α/2. When the first measurement unit 14 is active, the control computer 46 drives the first mirror 50 into the position shown in solid lines in FIG. 1, and when the second measurement unit 16 is active, the control computer 46 drives the first mirror 50 into the position shown in dashed lines in FIG. 1 (at 50'). Scanning may then be performed by tilting the first mirror 50 back and forth relative to the initial position assumed by the mirror 50 in the particular operation mode. It is needless to say that beam scanning may additionally, or alternatively, include tilting the second mirror 52 back and forth.

In certain embodiments, the value of the angle α is anywhere between 1 and 10 degrees and, for example, between 3 and 7 degrees. It is needless to say that these numerical values for the angle α are merely exemplary and in no way intended to be limiting.

In alternate embodiments, the second mirror 52 may be configured to be adjustable between different initial positions to accommodate the different angles of incidence of an incoming beam on the deflector device 42 and output the beam on the same optical axis regardless of the angle of incidence.

The invention claimed is:

1. A scanning optical system, comprising:
 a plurality of optical sources, each optical source configured to provide a beam of optical radiation;
 a deflector device disposed to receive and deflect the beams provided by the optical sources, the deflector device configured for a scanning operation on a beam of radiation traversing the deflector device to scan a target, the beams provided by the optical sources comprising:
  a first beam incident on the deflector device with a first orientation; and
  a second beam incident on the deflector device with a second orientation, the first orientation being different from the second orientation;
 a plurality of interferometric measuring devices configured to optically analyze the target by establishing interference between radiation backscattered from the target and reference radiation obtained from at least one of the beams provided by the optical sources; and
 a control computer configured to control the deflector device to:
  perform the scanning operation during operation of a first measuring device; and
  inactivate the scanning operation during operation of a second measuring device.

2. The scanning optical system of claim 1, wherein:
 the deflector device includes a first scanning mirror disposed for tilting about at least one tilt axis; and
 the first beam is incident on the first scanning mirror with the first orientation and the second beam is incident on the first scanning mirror with the second orientation.

3. The scanning optical system of claim 1, wherein:
 the deflector device includes a first scanning mirror disposed for tilting about a first tilt axis and a second scanning mirror disposed for tilting about a second tilt axis;
 the first tilt axis is oriented perpendicularly to the second tilt axis;
 the first and second beams are incident on the first scanning mirror with the first and second orientations, respectively; and
 the first scanning mirror is arranged to direct the first and second beams to the second scanning mirror with a common, third orientation.

4. The scanning optical system of claim 1, wherein:
 the first measuring device comprises an OCT-based measuring unit; and
 the second measuring device comprises an OLCR-based measuring unit.

5. The scanning optical system of claim 1, wherein at least one of the measuring devices comprises a measuring unit configured to perform at least one of the following: a function for measuring an axial length of an eye, a function for measuring a central thickness of a cornea, a function for measuring an axial length of an anterior chamber of an eye, a function for measuring a central thickness of a crystal lens of an eye, a function for performing a keratometry of an eye, a function for measuring a white-to-white distance of an eye, a function for performing a pupillometry of an eye, a function for measuring an eccentricity of a visual axis of an eye, and a function for measuring a retinal thickness of an eye.

6. The scanning optical system of claim 1, wherein at least one of the measuring devices includes a measuring unit configured to perform at least one of two-dimensional and three-dimensional imaging of an eye structure.

7. The scanning optical system of claim 1, wherein the plurality of optical sources is two.

8. The scanning optical system of claim 1, wherein the plurality of optical sources is three.

* * * * *